(12) United States Patent
Hunt

(10) Patent No.: US 11,583,693 B2
(45) Date of Patent: Feb. 21, 2023

(54) THERAPEUTIC FURNITURE APPARATUS

(71) Applicant: John R. Hunt, Cuyahoga Falls, OH (US)

(72) Inventor: John R. Hunt, Cuyahoga Falls, OH (US)

( * ) Notice: Subject to any disclaimer, the term of this patent is extended or adjusted under 35 U.S.C. 154(b) by 819 days.

(21) Appl. No.: 16/582,292

(22) Filed: Sep. 25, 2019

(65) Prior Publication Data

US 2020/0108267 A1    Apr. 9, 2020

Related U.S. Application Data

(60) Provisional application No. 62/743,154, filed on Oct. 9, 2018.

(51) Int. Cl.
*A61N 2/06* (2006.01)
*A47C 31/00* (2006.01)

(52) U.S. Cl.
CPC .............. *A61N 2/06* (2013.01); *A47C 31/003* (2013.01); *A61H 2201/10* (2013.01)

(58) Field of Classification Search
CPC .......... A61N 2/00; A61N 2/004; A61N 2/006; A61N 2/008; A61N 2/06; A47C 31/003
See application file for complete search history.

(56) References Cited

U.S. PATENT DOCUMENTS

| 4,537,181 A * | 8/1985 | Shalhoob ................. | A61N 2/12 600/9 |
| 7,163,505 B1 * | 1/2007 | Cancio ..................... | A61N 2/12 600/9 |
| 2013/0225908 A1 * | 8/2013 | Jacobson ............... | A61N 2/008 600/13 |
| 2015/0375005 A1 * | 12/2015 | Segal ..................... | A61N 2/006 600/13 |

FOREIGN PATENT DOCUMENTS

DE              3938920        *  5/1991  .............. A61N 2/02

* cited by examiner

*Primary Examiner* — Carrie R Dorna
(74) *Attorney, Agent, or Firm* — Eschweiler & Potashnik, LLC

(57) ABSTRACT

Various embodiments of the present disclosure are directed towards a therapeutic furniture apparatus. The therapeutic furniture apparatus includes a non-magnetic base. The non-magnetic base has a vertical portion that extends vertically from the base, and a horizontal portion that extends from the vertical portion at a first location over the non-magnetic base. A non-magnetic ring attachment structure is coupled to the horizontal portion of the non-magnetic support structure at a second location disposed directly over the non-magnetic base. The non-magnetic ring attachment structure extends from the horizontal portion toward the non-magnetic base. A plurality of non-magnetic ring structures are coupled to the non-magnetic ring attachment structure and disposed between the horizontal portion of the non-magnetic support structure and the non-magnetic base. A plurality of permanent magnets are disposed at regular intervals on each of the plurality of non-magnetic ring structures.

11 Claims, 5 Drawing Sheets

THERAPEUTIC FURNITURE APPARATUS

REFERENCE TO RELATED APPLICATION

This application claims the benefit of U.S. Provisional Application No. 62/743,154, filed on Oct. 9, 2018, the contents of which are hereby incorporated by reference in their entirety.

BACKGROUND

Magnetic therapy is an alternative medical practice that uses magnets to alleviate pain and other health concerns. The magnets produce magnetic fields. By placing a user (e.g., a human) within the magnetic fields, magnetic forces are exerted on the user. The magnetic forces exerted on the user may provide relief to the user's ailment (e.g., muscle relaxation, joint pain relief, mental relaxation, etc.). Some examples of magnetic therapy devices are bracelets having one or more magnets, rings having one or more magnets, or the like.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1A:
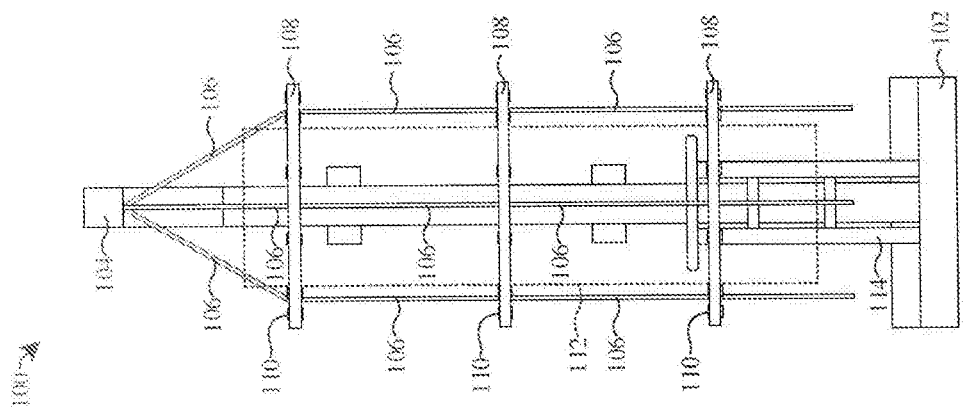
FIGS. 1A-1C illustrate various view of some embodiments of a therapeutic furniture apparatus.

The present disclosure will now be described with reference to the drawings wherein like reference numerals are used to refer to like elements throughout, and wherein the illustrated structures are not necessarily drawn to scale. It will be appreciated that this detailed description and the corresponding figures do not limit the scope of the present disclosure in any way, and that the detailed description and figures merely provide a few examples to illustrate some ways in which the inventive concepts can manifest themselves.

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

In various embodiments, the present application is directed toward a therapeutic furniture apparatus. In some embodiments, the therapeutic furniture apparatus provides a user (e.g., a human) with muscle (e.g., quadriceps femoris, psoas major, etc.), joint (e.g., hip joints, knee joints, etc.), and/or mind relaxation.

In some embodiments, the user may obtain muscle, joint, and/or mind relaxation by sitting or standing on the therapeutic furniture apparatus and having a plurality of magnetic fields pass through the user's body. For example, the user may stand on a base of the therapeutic furniture apparatus. Depending on an ailment of the user (e.g., muscle pain, joint pain, migraines, etc.), the user may adjust a plurality of rings, each of the adjustable rings comprising a plurality of magnets. By adjusting the plurality of rings, the user may alter a shape, strength, and/or location of the magnetic fields over the base of the therapeutic furniture apparatus. By altering the magnetic fields over the base of the therapeutic furniture apparatus, the user may focus the magnetic fields on specific areas of the user's body. By focusing the magnetic fields on specific areas of the user's body, a defined magnetic field may pass through the user to provide relief (e.g., relaxation of a muscle, pain relief of a joint, mental relaxation, etc.) for the user's ailment. In some embodiments, the defined magnetic field may provide relief for the user's ailment due to the defined magnetic field exerting a magnetic force on the user's body (e.g., red blood cells of the user) that causes a therapeutic response by the user's body.

Figure 1B:
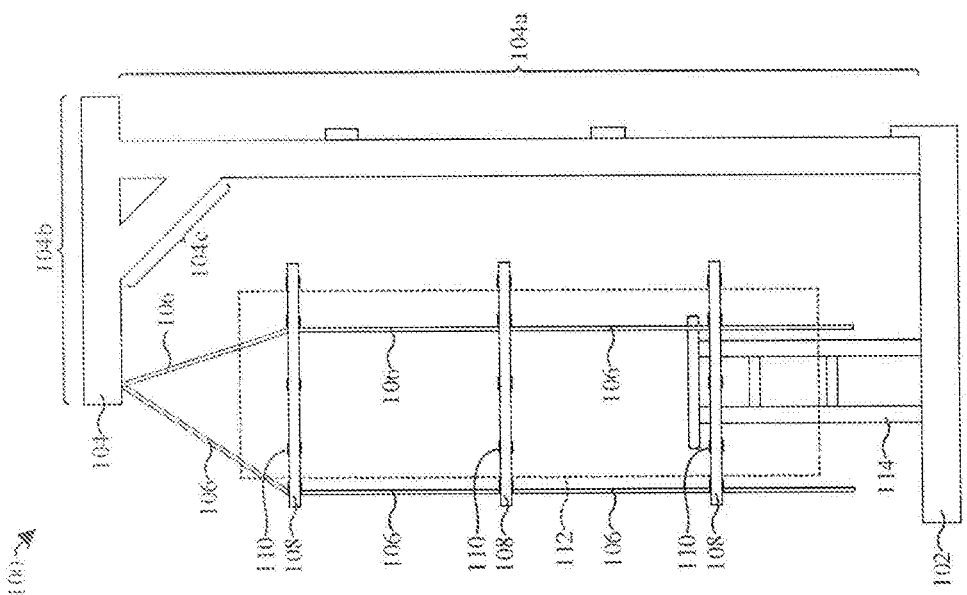
Figure 1C:
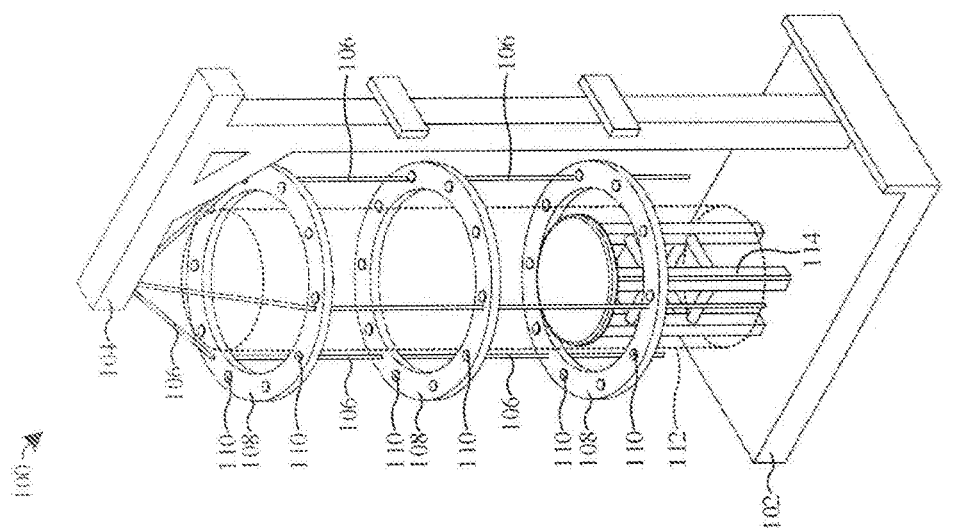

FIGS. 1A-1C illustrate various views of some embodiments of a therapeutic furniture apparatus 100. FIG. 1A illustrates an isometric view of some embodiments of the therapeutic furniture apparatus 100 of FIGS. 1B-1C. FIG. 1B illustrates a side view of some embodiments of the therapeutic furniture apparatus 100 of FIG. 1A. FIG. 1C illustrates a front view of some embodiments of the therapeutic furniture apparatus 100 of FIG. 1A.

As shown in FIGS. 1A-1C, the therapeutic furniture apparatus 100 comprises a base 102. In some embodiments, the base 102 is made of a non-magnetic material. In such embodiments, the base 102 is referred to as a non-magnetic base. In further embodiments, the base 102 is made of, for example, wood (e.g., pine, oak, etc.), a polymer (e.g., polyethylene, polypropylene, etc.), some other non-magnetic material, or a combination of the foregoing. In yet further embodiments, the base 102 comprises a first edge, a second edge spaced from the first edge in a first lateral direction, a third edge, and a fourth edge spaced from the third edge in a second lateral direction perpendicular to the first lateral direction.

A first portion of the base 102 may extend vertically from a second portion of the base 102, such that an upper surface of the first portion of the base 102 is disposed over an upper surface of the second portion of the base 102. In some embodiments, the first portion of the base 102 may at least partially define a first sidewall of the base 102. In further embodiments, the first portion of the base 102 and the second portion of the base 102 may be distinct structures (e.g., separate pieces of wood). In such embodiments, the first portion of the base 102 is affixed to the second portion of the base 102 by, for example, screws, nails, an adhesive (e.g., glue, epoxy, etc.), some other fastener/fixative, or a combination of the foregoing. In further such embodiments, the first portion of the base 102 and the second portion of the base 102 contact one another at a connection joint (e.g., butt joint, rabbet joint, etc.). In other embodiments, the first portion of the base 102 and the second portion of the base 102 are a single structure (e.g., a single piece of molded plastic).

A support structure 104 is disposed on the base 102. In some embodiments, the support structure 104 is made of a non-magnetic material. In such embodiments, the support structure 104 is referred to as a non-magnetic support structure. In further embodiments, the support structure 104 is made of, for example, wood (e.g., pine, oak, etc.), a polymer (e.g., polyethylene, polypropylene, etc.), some other non-magnetic material, or a combination of the foregoing.

The support structure 104 is affixed to the base 102. In some embodiments, the support structure 104 may be affixed to the base 102 by, for example, screws, nails, an adhesive (e.g., wood, epoxy, etc.), some other fastener/fixative, or a combination of the foregoing. In further embodiments, the support structure 104 contacts the base 102 at a connection joint (e.g., butt joint, mortise and tenon, etc.).

The support structure 104 comprises a vertical portion 104a and a horizontal portion 104b. The vertical portion 104a extends vertically from the base 102 to a height. The horizontal portion 104b extends horizontally from the vertical portion 104a and directly over the base 102. In some embodiments, the vertical portion 104a and the horizontal portion 104b are distinct structures. In such embodiments, the horizontal portion 104b is affixed to the vertical portion 104a by, for example, screws, nails, an adhesive (e.g., wood, epoxy, etc.), some other fastener/fixative, or a combination of the foregoing. In further such embodiments, the vertical portion 104a and the horizontal portion 104b contact one another at a connection joint (e.g., dado joint, a lap joint, etc.). In other embodiments, the vertical portion 104a and the horizontal portion 104b are portions of a single structure.

In some embodiments, the support structure 104 comprises an angled portion 104c. The angled portion 104c extends from the vertical portion 104a to the horizontal portion 104b to provide increased structural support for the horizontal portion 104b. In some embodiments, the angled portion 104c is a distinct structure. In such embodiments, the angled portion 104c is affixed to the vertical portion 104a and the horizontal portion 104b by, for example, screws, nails, an adhesive (e.g., wood, epoxy, etc.), some other fastener/fixative, or a combination of the foregoing. In further such embodiments, the angled portion 104c may contact the vertical portion 104a and the horizontal portion 104b at connection joints (e.g., butt joints, mortise and tenon, etc.). In other embodiments, the vertical portion 104a, the horizontal portion 104b, and the angled portion 104c are portions of a single structure.

A ring attachment structure 106 is coupled to the support structure 104. In some embodiments, the ring attachment structure 106 is coupled to the horizontal portion 104b of the support structure 104. The ring attachment structure 106 is coupled to the support structure 104 at a point disposed directly over the base 102, such that the ring support structure hangs directly over the base 102.

In some embodiments, the ring attachment structure 106 is coupled to a coupling assembly (not shown in FIGS. 1A-1C) that is affixed to the support structure 104 (e.g., via screws, nails, an adhesive, etc.). The coupling assembly is affixed to a point on the horizontal portion 104b disposed directly over the base 102, such that a vertical axis extending downwardly from the coupling assembly intersects the base 102. The coupling assembly is configured to rotate 360 degrees about the vertical axis in a clockwise direction and/or a counterclockwise direction. Because the coupling assembly is configured to rotate 360 degrees, the ring attachment structure 106 may be rotated 360 degrees by a user (e.g., a human) about the vertical axis in a clockwise direction and/or a counterclockwise direction.

In some embodiments, the ring attachment structure 106 is made of a non-magnetic material. In such embodiments, the ring attachment structure 106 is referred to as a non-magnetic ring attachment structure. In further embodiments, the ring attachment structure 106 comprises a plurality of non-magnetic strings/ropes (e.g., nylon strings/ropes, natural fiber strings/ropes, etc.). In further embodiments, the ring attachment structure 106 comprises less than or equal to three non-magnetic strings/ropes. The ring attachment structure 106 may consist of three non-magnetic strings/ropes. In yet further embodiments, the non-magnetic strings/ropes may be referred to as connector structures.

A plurality of ring structures 108 are coupled to the ring attachment structure 106. In some embodiments, the ring structures 108 are made of a non-magnetic material. In such embodiments, the ring structures 108 are referred to as non-magnetic ring structures. In further embodiments, the ring structures 108 are made of, for example, wood (e.g., pine, oak, etc.), a polymer (e.g., polyethylene, polypropylene, etc.), some other non-magnetic material, or a combination of the foregoing. In further embodiments, the ring structures 108 may comprise less than or equal to three individual ring structures. The ring structures 108 may consist of three individual rings. In yet further embodiment, each of the ring structures 108 may be a circular-shaped ring structure. In other embodiments, each of the ring structures 108 may have some other geometrically-shaped ring structure (e.g., a square ring, a triangular ring, etc.).

A plurality of permanent magnets 110 (e.g., rare-earth magnets) are coupled to each of the ring structures 108. For example, a first plurality of permanent magnets are coupled to a first ring structure of the plurality of ring structures 108, a second plurality of permanent magnets are coupled to a second ring structure of the plurality of ring structures 108, and a third plurality of permanent magnets are coupled to a third ring structure of the plurality of ring structures 108. In some embodiments, the permanent magnets 110 are disposed on or in the ring structures 108. The permanent magnets 110 are disposed at regular intervals on or in a corresponding one of the ring structures 108 (e.g., spaced a substantially similar distance apart). For example, the permanent magnets of the first plurality of permanent magnets are disposed at regular intervals on or in the first ring structure.

An area within the ring structures 108 is a therapy space 112. In some embodiments, the therapy space 112 extends below a lowermost ring structure and/or above an uppermost ring structure of the ring structures 108. The permanent magnets 110 generate defined magnetic fields within the therapy space 112.

The permanent magnets 110 are arranged to provide a user (e.g., a human) with a pre-determined magnetic field configuration within the therapy space 112, such that the user can receive magnetic therapy from the therapeutic furniture apparatus 100. For example, depending on an ailment of the user (e.g., muscle pain, joint pain, migraines, etc.) and the location of the ailment (e.g., lower extremity, upper extremity, torso, head, etc.), the user may adjust the ring structures 108 to alter a shape, a strength, and/or a location of the defined magnetic fields over the base 102. The user may adjust the ring structures 108 by moving one or more of the ring structures 108 upward on the ring attachment structure 106, by moving one or more of the ring structures 108 downward on the ring attachment structure 106, or by tilting the one or more of the ring structures 108 at an angle on the ring attachment structure 106. By altering the magnetic fields over the base 102, the user may focus the magnetic fields on a specific area(s) of the user's body. By focusing the magnetic fields on specific area(s) of the user's body, the defined magnetic field may pass through the user to provide relief for the user's specific ailment. Once the ring structures 108 are adjusted to the user's needs, the user has set the pre-determined magnetic field configuration within the therapy space 112 for the user.

Once the pre-determined magnetic field configuration is set, the user may stand on the base 102 within the therapy space 112. It will be appreciated that the user may set the pre-determined magnetic field configuration while the user is in the therapy space 112. Once inside the therapy space 112, the user may rotate the ring attachment structure 106, such that the ring structures 108 and the permanent magnets 110 rotate 360 degrees around the user. In some embodiments, the user may rotate the ring attachment structure 106 by hand (e.g., by the user's own force). In other embodiments, the user may rotate the ring attachment structure 106 by activating (e.g., via a switch) a motor (e.g., an electric motor) that rotates the ring attachment structure 106. By rotating the permanent magnets 110 around the user, the user causes the magnetic flux lines of the defined magnetic field to pass through the user's body in varying directions (e.g., causing magnetic flux lines having opposing directions to alternatingly pass through the user as the user rotates the ring attachment structure 106). In some embodiments, the pre-determined magnetic field configuration may provide relief (e.g., relaxation of a muscle, pain relief of a joint, mental relaxation, etc.) for the user's ailment due to the defined magnetic field of the pre-determined magnetic field configuration exerting a magnetic force on the user's body that causes a therapeutic response by the user's body. In further embodiments, relief for the user's ailment may be provided due to the magnetic flux lines of the defined magnetic field of the pre-determined magnetic field configuration passing through the user's body in varying directions as the permanents magnets 110 rotate around the user.

In some embodiments, the therapeutic furniture apparatus 100 comprises a seat 114. In some embodiments, the seat 114 is made of a non-magnetic material. In such embodiments, the seat 114 is referred to as a non-magnetic seat. In further embodiments, the seat 114 is made of, for example, wood (e.g., pine, oak, etc.), a polymer (e.g., polyethylene, polypropylene, etc.), some other non-magnetic material, or a combination of the foregoing. The seat 114 allows a user to sit in the therapy space 112, such that the user can receive magnetic therapy while sitting down. The seat 114 may be used by a user who is unable to stand in the therapy space 112 during the magnetic therapy. In further embodiments, the seat 114 is affixed to the base 102 (e.g., via screws, nails, an adhesive, etc.). In other embodiments, the seat 114 may not be affixed to the base 102 (e.g., removable from the base). In yet further embodiments, the seat 114 may be, for example, a stool, a chair, or the like. It will be appreciated that, in some embodiments, the therapeutic furniture apparatus 100 may not comprise the seat 114.

Figure 2:
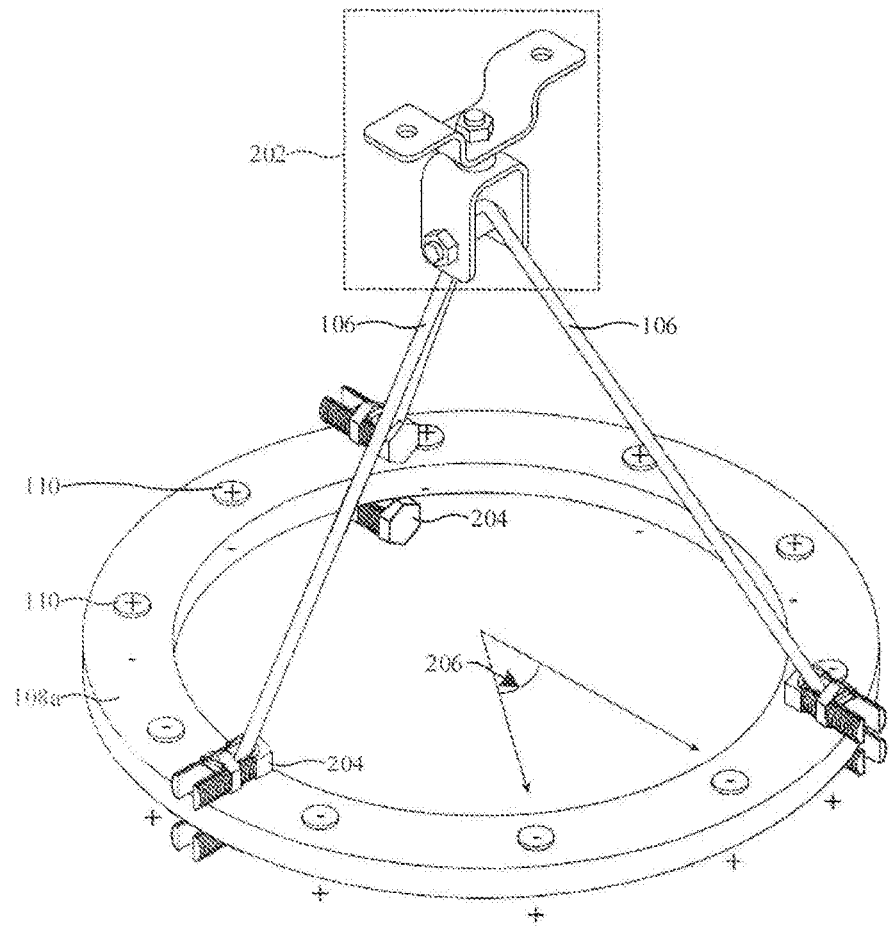
FIG. 2 illustrates a perspective view of some embodiments of one of the ring structures coupled to the ring attachment structure of the therapeutic furniture apparatus of FIGS. 1A-1C.

FIG. 2 illustrates a perspective view of some embodiments of one of the ring structures 108 coupled to the ring attachment structure 106 of the therapeutic furniture apparatus 100 of FIGS. 1A-1C. For example, FIG. 2 illustrates a first ring structure 108a of the plurality of ring structures 108 coupled to the ring attachment structure 106. It will be appreciated that, in some embodiments, each of the ring structures 108 may comprise features (e.g., structural features, functional features, etc.) described below regarding the first ring structure 108a and/or each of the each of the permanent magnets 110 may comprise features described below regarding the permanent magnets 110 disposed on/in the first ring structure 108a.

As shown in FIG. 2, the ring attachment structure 106 is coupled to a coupling assembly 202. The coupling assembly 202 comprises an upper portion and a lower portion. The upper portion of the coupling assembly 202 is connected to the lower portion of the coupling assembly 202 via a first rod that extends vertically along a vertical axis. The upper portion of the coupling assembly 202 is configured to be affixed (e.g., via screws, nails, an adhesive, etc.) to the support structure 104. The lower portion of the coupling assembly 202 can rotate 360 degrees about the vertical axis in a clockwise direction and/or a counterclockwise direction. In some embodiments, the ring attachment structure 106 is coupled to a second rod of the lower portion of the coupling assembly 202. In further embodiments, a motor (not shown) (e.g., an electric motor) may be coupled to the coupling assembly 202. The motor is configured to rotate the ring attachment structure 106 about the vertical axis in a clockwise direction and/or a counterclockwise direction. In yet further embodiments, the user may activate the motor by pressing a switch (e.g., a foot activated switch) once inside the therapy space 112.

In some embodiments, the coupling assembly 202 is made of a non-magnetic material. In such embodiments, the coupling assembly 202 is referred to as a non-magnetic coupling assembly. For example, the coupling assembly 202 may be made of copper, aluminum, wood, nylon, a polymer, some other non-magnetic material, or a combination of the foregoing.

In some embodiments, the ring structures 108 may comprise a plurality of openings that the ring attachment structure 106 passes through, such that ring structures 108 can be coupled to the ring attachment structure 106. For example, the ring structures 108 may comprise a plurality of openings that the plurality of non-magnetic strings/ropes pass through. The ring attachment structure 106 comprises a plurality of ring holding structures 204. The ring holding structures 204 are disposed below each of the ring structures 108. In some embodiments, the ring holding structures 204 are disposed above and below each of the ring structures 108. The ring holding structures 204 provide a means to hold the ring structures 108 in place along the ring attachment structure 106. For example, a first set of ring holding structures may be disposed below (and above) the first ring structure 108a. The first set of ring holding structures hold the first ring structure 108a in place along the ring attachment structure 106.

In some embodiments, the ring holding structures 204 are made of a non-magnetic material. In such embodiments, the ring holding structures 204 are referred to as non-magnetic ring holding structures. For example, the ring holding structures 204 may be made of copper, aluminum, wood, nylon, a polymer, some other non-magnetic material, or a combination of the foregoing.

In some embodiments, the ring holding structures 204 may be, for example, knots (e.g., knots tied in the non-magnetic strings/ropes), non-magnetic clamps, split-bolt connectors, or the like. In further embodiments, the ring holding structures 204 are copper comprising split-bolt connectors. In further embodiments, the ring holding structures 204 may be adjustable (e.g., allowing the ring structures 108 to be tilted/moved up/move down the ring attachment structure 106). In other embodiments, the ring holding structures 204 may be fixed (e.g., the non-magnetic strings/ropes may be glued to the ring structures 108 preventing adjustment of the ring structures 108).

In some embodiments in which the ring holding structures 204 are adjustable, the user may adjust the ring holding structures 204 (e.g., by unscrewing the one or more of the split-bolt connectors) to move the ring holding structures 204 independently up or down the ring attachment structure 106. By moving the ring holding structures 204 independently up or down the ring attachment structure 106, the user may adjust the ring holding structures 204 to move one or more of the ring structures 108 up the ring attachment structure 106, move one or more of the ring structures 108 down the ring attachment structure 106, and/or tilt one or more of the ring structures 108 in relation to an upper surface of the base 102. For example, the user may adjust the first set of ring holding structures 204 to tilt the first ring structure 108a at a 45-degree angle (or some other angle) in relation to the upper surface of the base 102. After the user adjusts the ring structures 108, the user may secure the ring structures 108 in their adjusted places (e.g., by screwing in the split-bolt connectors) by securing the ring holding structures 204 to the ring attachment structure 106.

In some embodiments, a number of the permanent magnets 110 disposed on/in the first ring structure 108a (hereinafter referred to as "permanent magnets 110 of the first ring structure 108a") is even. In further embodiments, less than or equal to 10 permanent magnets 110 are disposed on/in the first ring structure 108a. In yet further embodiments, 10 permanent magnets 110 are disposed on/in the first ring structure 108a.

In some embodiments, a first half of the permanent magnets 110 of the first ring structure 108a are positioned so that their positive polarity sides (e.g., south poles) are facing upward (e.g., away from the base 102), and a second half of the permanent magnets 110 of the first ring structure 108a are positioned so that their negative polarity sides (e.g., north poles) are facing upward (e.g., away from the base 102). In further embodiments, the first half of the permanent magnets 110 are all disposed on one side of the first ring structure 108a, and the second half of the permanent magnets 110 are all disposed on another side of the first ring structure 108a. For example, if 10 permanent magnets 110 are disposed on/in the first ring structure 108a, 5 of the 10 permanent magnets are positioned on a first side of the first ring structure 108a with their positive polarity sides facing away from the base 102, and 5 of the 10 permanent magnets are positioned on a second side of the first ring structure 108a with their negative polarity sides facing away from the base 102.

In some embodiments, the permanent magnets 110 of the first ring structure 108a are disposed on/in the first ring structure 108a by, for example, friction (e.g., a press fitting), an adhesive, or the like. In further embodiments, the permanent magnets 110 of the first ring structure 108a may extend completely through the first ring structure 108a, such that each of the permanent magnets 110 of the first ring structure 108a have an upper portion disposed above an upper surface of the first ring structure 108a, a lower portion disposed below a lower surface of the first ring structure 108a, and a central portion disposed between the upper surface and lower surface of the first ring structure 108a. In other embodiments, the permanent magnets 110 of the first ring structure 108a may have upper surfaces that are co-planar with the upper surface of the first ring structure 108a and lower surfaces that are co-planar with the lower surface of the first ring structure 108a. In yet other embodiments, the permanent magnets 110 of the first ring structure 108a may extend partially through the first ring structure 108a. For example, recesses may be disposed in the first ring structure 108a that extend only partially into the first ring structure 108a, and the permanent magnets 110 may be press fit (and/or glued) into the recesses.

In some embodiments, the first ring structure 108a has an outer diameter of less than or equal to 30 inches. In further embodiments, the first ring structure 108a may have an outer diameter of 30 inches or 24 inches. The first ring structure 108a may have an inner diameter of less than or equal to 24 inches. In some embodiments in which the first ring structure 108a has an outer diameter of 24 inches, the first ring structure 108a has an inner diameter of 18 inches. In some embodiments in which the first ring structure 108a has an outer diameter of 30 inches, the first ring structure 108a has an inner diameter of 24 inches or 22 inches. In yet further embodiments, a ring thickness of the first ring structure 108a (e.g., between an inner perimeter of the first ring structure 108a and an outer perimeter of the first ring structure 108a) is less than or equal to 4 inches.

In some embodiments, each of the permanent magnets 110 of the first ring structure 108a are spaced an equal distance from a center of point of the first ring structure 108a (e.g., a center point of the outer diameter of the first ring structure 108a). In further embodiments, each of the permanent magnets 110 of the first ring structure 108a are spaced an equal distance from one another on the first ring structure 108a. In yet further embodiments, each of the permanent magnets 110 of the first ring structure 108a are spaced an equal distance from the inner diameter of the first ring structure 108a and spaced an equal distance from the outer diameter of the first ring structure 108a.

In some embodiments, the permanent magnets 110 are neodymium magnets. In further embodiments, each of the permanent magnets 110 are grade 52 neodymium magnets (e.g., N52 magnets). Each of the permanent magnets 110 may have a residual flux density greater than 14,500 gauss. In further embodiments, each of the permanent magnets 110 has a residual flux density between 14,500 gauss and 14,800 gauss. Each of the permanent magnets 110 may have a thickness (e.g., between an upper surface and a bottom surface) of 1 inch. In yet further embodiments, each of the permanent magnets 110 may have a diameter of 1 inch.

An angle 206 exists between neighboring magnets of the permanent magnets 110 of the first ring structure 108a. The angle 206 has a vertex at the center point of the first ring structure 108a. In some embodiments, the angle 206 is the same between each pair of neighboring magnets of the permanent magnets 110 of the first ring structure 108a. In further embodiments, the angle 206 may be less than or equal to about 36 degrees (e.g., +/−2.77 percent of 36 degrees). In yet further embodiments, the angle 206 is 36 degrees.

Figure 3:
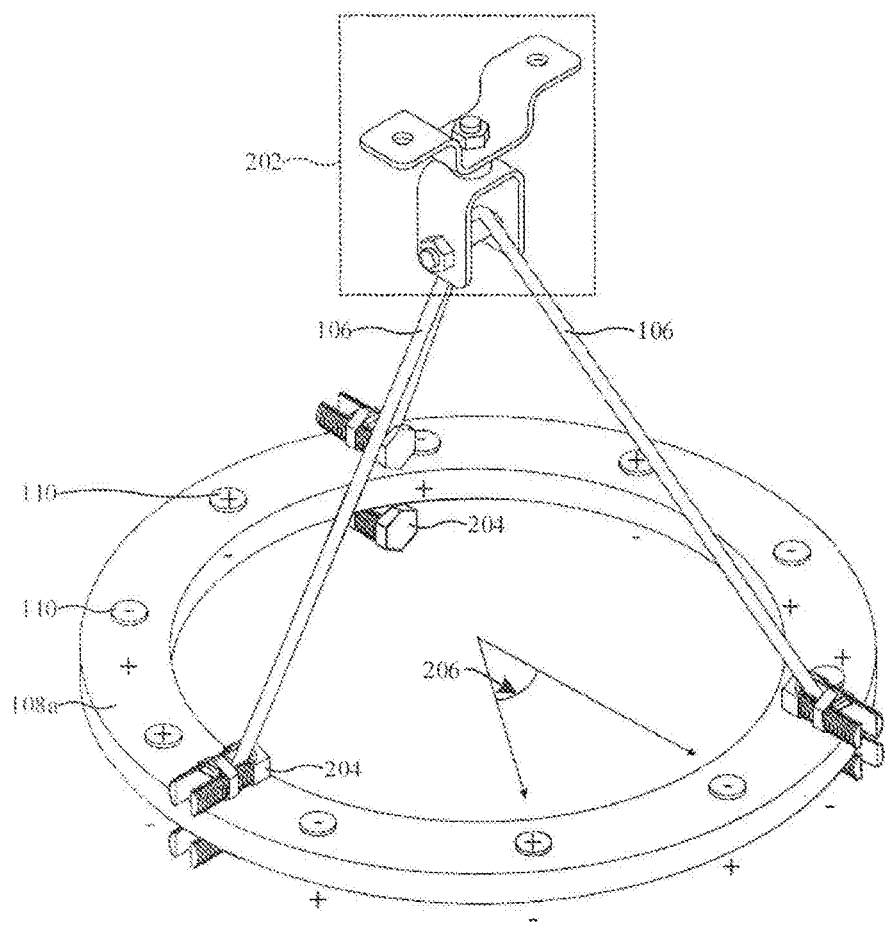
FIG. 3 illustrates a perspective view of some other embodiments of the one of the ring structures coupled to the ring attachment structure of the therapeutic furniture apparatus of FIG. 2.

FIG. 3 illustrates a perspective view of some other embodiments of the one of the ring structures 108 coupled to the ring attachment structure 106 of the therapeutic furniture apparatus 100 of FIG. 2.

As shown in FIG. 3, the permanent magnets 110 of the first ring structure 108a are positioned so that the sides (e.g., positive/negative polarity side) of the permanent magnets 110 of the first ring structure 108a facing upward alternate around the first ring structure 108a. For example, the permanent magnets 110 of the first ring structure 108a comprise a first permanent magnet, a second permanent magnet, a third permanent magnet, and a fourth permanent magnet. The second permanent magnet is disposed directly between the first permanent magnet and the third permanent magnet. The third permanent magnet is disposed directly between the fourth permanent magnet and the second permanent magnet. The first permanent magnet is positioned such that the positive polarity side (e.g., south pole) of the first permanent magnet is facing upward, the second permanent magnet is positioned such that the negative polarity side (e.g., north pole) of the second permanent magnet is facing upward, the third permanent magnet is positioned such that the positive polarity side (e.g., south pole) of the third permanent magnet is facing upward, and the fourth permanent magnet is positioned such that the negative polarity side (e.g., north pole) of the fourth permanent magnet is facing upward. This alternating pattern is repeated around the first ring structure 108a, such that no two magnets disposed directly next to one another have a same side (e.g., positive/negative polarity side) facing upward. In some embodiments, the plus signs (+) in FIGS. 2-3 indicate the positive polarity sides of the permanent magnets 110, and the negative signs (−) in FIGS. 2-3 indicate the negative polarity sides of the permanent magnets 110.

Figure 4:
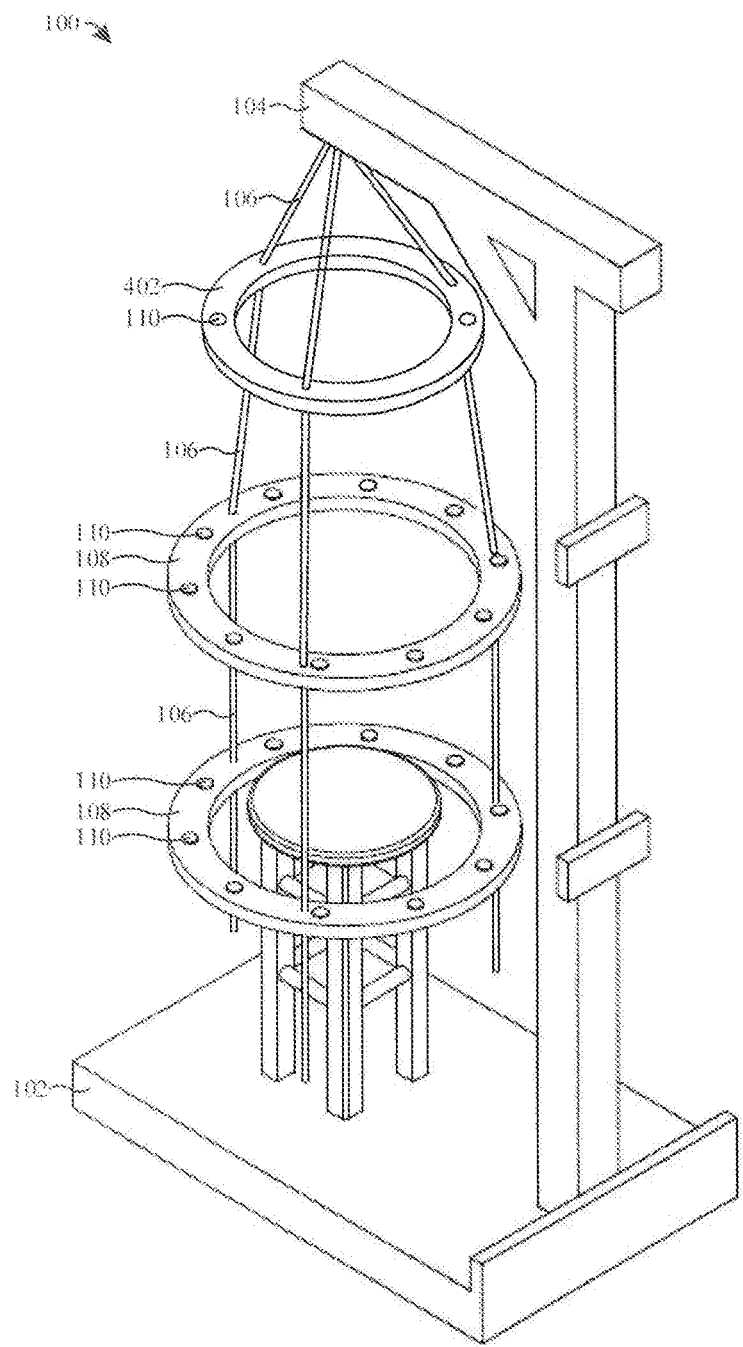
FIG. 4 illustrates an isometric view of some other embodiments of the therapeutic furniture apparatus of FIGS. 1A-1C.

FIG. 4 illustrates an isometric view of some other embodiments of the therapeutic furniture apparatus 100 of FIGS. 1A-1C.

As shown in FIG. 4, the therapeutic furniture apparatus 100 comprises a spacer ring structure 402. The spacer ring structure 402 is coupled to the ring attachment structure 106 (e.g., via openings and ring holding structures). In embodiments in which the ring attachment structure 106 comprises a plurality of non-magnetic strings/ropes, the spacer ring structure 402 spaces out the non-magnetic strings/ropes to prevent the non-magnetic strings/ropes from interfering with the user during use of the therapeutic furniture apparatus 100.

In some embodiments, the spacer ring structure 402 is made of a non-magnetic material. In such embodiments, the spacer ring structure 402 is referred to as a non-magnetic spacer ring structure. In further embodiments, the spacer ring structure 402 is made of, for example, wood (e.g., pine, oak, etc.), a polymer (e.g., polyethylene, polypropylene, etc.), some other non-magnetic material, or a combination of the foregoing. In yet further embodiments, the base 102, the support structure 104, the ring structures 108, the seat 114, and the spacer ring structure 402 are made of a same material. For example, the base 102, the support structure 104, the ring structures 108, the seat 114, and the spacer ring structure 402 may be made of a same wood material (e.g., oak).

In some embodiments, the spacer ring structure 402 has an outer diameter that is less than an outer diameter of each of the ring structures 108. The spacer ring structure 402 may have an outer diameter less than or equal to 18 inches. The spacer ring structure 402 may have an inner diameter of less than or equal to 12 inches. In further embodiments, the spacer ring structure 402 may have an outer diameter of 18 inches and an inner diameter of 12 inches. In yet further embodiments, a ring thickness of the spacer ring structure 402 (e.g., between an inner perimeter and an outer perimeter) is less than or equal to 4 inches.

In some embodiments, one or more of the permanent magnets 110 may be coupled to the spacer ring structure 402. In some embodiments, the one or more of the permanent magnets 110 are disposed on or in the spacer ring structure 402. In further embodiments, the one or more of the permanent magnets 110 are disposed on/in the spacer ring structure 402 by, for example, friction (e.g., a press fitting), an adhesive, or the like. The one or more of the permanent magnets 110 disposed on/in the spacer ring structure 402 may extend through the spacer ring structure 402.

A number of permanent magnets 110 disposed on/in the spacer ring structure 402 may be less than a number of permanent magnets 110 disposed on/in each of the ring structures 108. In some embodiments, the number of the permanent magnets 110 disposed on/in the spacer ring structure 402 is even. In further embodiments, the number of permanent magnets 110 disposed on/in the spacer ring structure 402 is less than or equal to 4 permanent magnets 110. In further embodiments, the number of permanent magnets 110 disposed on/in the spacer ring structure 402 is 4 permanent magnets or 2 permanent magnets. In other embodiments, no permanent magnets 110 are disposed on/in the spacer ring structure 402.

Figure 5:
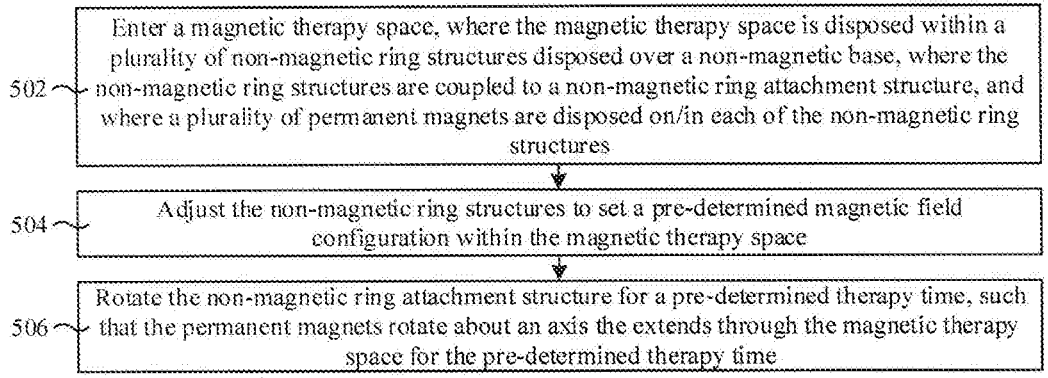
FIG. 5 illustrates a flowchart of some embodiments of a method for performing a magnetic therapy on a user with a therapeutic furniture apparatus.

FIG. 5 illustrates a flowchart of some embodiments of a method for performing a magnetic therapy on a user with a therapeutic furniture apparatus. While the flowchart 500 of FIG. 5 is illustrated and described herein as a series of acts or events, it will be appreciated that the illustrated ordering of such acts or events is not to be interpreted in a limiting sense. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

At act 502, a magnetic therapy space is entered, where the magnetic therapy space is disposed within a plurality of non-magnetic ring structures disposed over a non-magnetic base, where the non-magnetic ring structures are coupled to a non-magnetic ring attachment structure, and where a plurality of permanent magnets are disposed on/in each of the non-magnetic ring structures.

For example, a user (e.g., a human) may enter the magnetic therapy space. The user may enter the magnetic therapy space by stepping on to a non-magnetic base; lifting a bottommost non-magnetic ring of the plurality of non-magnetic rings over the user's head; and lowering the bottommost non-magnetic ring around the user, such that the user is standing (or sitting) within inner perimeters of the non-magnetic rings.

At act 504, the non-magnetic ring structures are adjusted to set a pre-determined magnetic field configuration within the magnetic therapy space.

For example, the user may adjust the non-magnetic ring structures by disengaging (e.g., unscrewing) ring holding structures for one of the non-magnetic ring structures, such that the one of the non-magnetic ring structures may be tilted at an angle, moved up, or moved down. After the one of the non-magnetic ring structures is tilted or moved up/down, the user may engage (e.g., screw in) the ring holding structures for the one of the non-magnetic ring structures, such that the one of the non-magnetic ring structures is held in its adjusted position on the non-magnetic ring attachment structure. This process is repeated until each of the non-magnetic rings are adjusted to the user's specific needs.

The user may adjust the non-magnetic rings based on a specific ailment of the user. For example, if the user's specific ailment is knee pain, the user may lower one or more of the non-magnetic rings, such that the one or more of the non-magnetic rings is arranged around the user's knee. In addition, the user may tilt the one or more of the non-magnetic rings at an angle in relation to the user's knee. On the other hand, if the user's ailment is upper back pain, the user may raise one or more of the non-magnetic rings, such that the one or more of the non-magnetic rings is arranged around the user's upper back. In addition, the user may tilt the one or more of the non-magnetic rings at an angle in relation to the user's torso.

At act 506, the non-magnetic ring attachment structure is rotated for a pre-determined therapy time, such that the permanent magnets rotate about an axis the extends through the magnetic therapy space for the pre-determined therapy time.

For example, the user may rotate the non-magnetic ring-attachment structure by hand, such that the permanent magnets rotate around the user. In other embodiments, the user may activate a motor (e.g., an electric motor) to rotate the non-magnetic ring-attachment structure, thereby causing the permanent magnets to rotate around the user. In further embodiments, while the user is in the magnetic therapy space, the user continues to rotate the non-magnetic ring-attachment structure for the pre-determined therapy time (e.g., 5 minutes, 10 minutes, 15 minutes, etc.). Because the permanent magnets rotate around the user for the pre-determined therapy time, the user may obtain relief for the user's specific ailment (e.g., relaxation of a muscle, pain relief of a joint, mental relaxation, etc.).

In some embodiments, the present application provides a therapeutic furniture apparatus. The therapeutic furniture apparatus comprises a non-magnetic base, the non-magnetic base having a first edge opposite a second edge. A non-magnetic support structure is disposed on the non-magnetic base. The non-magnetic support structure comprises a vertical portion that extends vertically from the non-magnetic base and comprises a horizontal portion that extends from the vertical portion at a first location disposed over the non-magnetic base. The horizontal portion extends horizontally over the non-magnetic base toward the first edge of the non-magnetic base. A non-magnetic ring attachment structure is coupled to the horizontal portion of the non-magnetic support structure at a second location disposed between the first edge and the second edge of the non-magnetic base, wherein the non-magnetic ring attachment structure extends from the horizontal portion of the non-magnetic support structure toward the non-magnetic base. A plurality of non-magnetic ring structures are coupled to the non-magnetic ring attachment structure, wherein the plurality of non-magnetic ring structures are disposed between the horizontal portion of the non-magnetic support structure and the non-magnetic base. A plurality of permanent magnets are disposed in each of the plurality of non-magnetic ring structures, each of the plurality of permanent magnets extending through one of the plurality of non-magnetic ring structures.

In some embodiments, the present application provides a furniture apparatus for providing magnetic therapy to a person. The furniture apparatus comprises a non-magnetic base. A non-magnetic support structure extends upwardly from the non-magnetic base. A coupling assembly is coupled to the non-magnetic support structure, wherein the coupling assembly is disposed at a first height directly over the non-magnetic base, wherein a vertical axis extends downwardly from the coupling assembly to the non-magnetic base, and wherein the coupling assembly is configured to rotate 360 degrees about the vertical axis in a clockwise direction and/or a counterclockwise direction. A first non-magnetic ring structure is suspended from the coupling assembly by connector structures, wherein the first non-magnetic ring structure is suspended so as to be axially symmetric about the vertical axis. A second non-magnetic ring structure is suspended from the first non-magnetic ring structure by the connector structures, wherein the second non-magnetic ring structure is axially symmetric about the vertical axis such that the first non-magnetic ring structure and the second non-magnetic ring structure collectively define a therapy space inside of which the person can reside to receive the magnetic therapy. A first plurality of permanent magnets are disposed at regular intervals on or in the first non-magnetic ring structure. A second plurality of permanent magnets are disposed at regular intervals on or in the second non-magnetic ring structure.

In some embodiments, the present application provides a method for performing a magnetic therapy on a user with a therapeutic furniture apparatus. The method comprises the user entering a magnetic therapy space, wherein the magnetic therapy space is disposed within a plurality of non-magnetic ring structures disposed directly over a non-magnetic base, wherein the plurality of non-magnetic ring structures are coupled to a non-magnetic ring attachment structure, and wherein a plurality of permanent magnets are disposed on or in each of the non-magnetic ring structures. The non-magnetic ring structures are adjusted to set a pre-determined magnetic field configuration within the magnetic therapy space for a specific ailment of the user. The non-magnetic ring attachment structure is rotated for a pre-determined therapy time, such that the plurality of permanent magnets rotate around the user for the pre-determined therapy time The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A furniture apparatus for providing magnetic therapy to a person, comprising:

a non-magnetic base;
a non-magnetic support structure extending upwardly from the non-magnetic base;
a coupling assembly coupled to the non-magnetic support structure, wherein the coupling assembly is disposed at a first height directly over the non-magnetic base, wherein a vertical axis extends downwardly from the coupling assembly to the non-magnetic base, and wherein the coupling assembly is configured to rotate 360 degrees about the vertical axis in a clockwise direction and a counterclockwise direction;
a first non-magnetic ring structure suspended from the coupling assembly by connector structures, wherein the first non-magnetic ring structure is suspended so as to be axially symmetric about the vertical axis;
a second non-magnetic ring structure suspended from the first non-magnetic ring structure by the connector structures, wherein the second non-magnetic ring structure is axially symmetric about the vertical axis such that the first non-magnetic ring structure and the second non-magnetic ring structure collectively define a therapy space inside of which the person can reside to receive the magnetic therapy;
a first plurality of permanent magnets disposed at regular intervals on or in the first non-magnetic ring structure; and
a second plurality of permanent magnets disposed at regular intervals on or in the second non-magnetic ring structure.

2. The furniture apparatus of claim 1, wherein:
the first plurality of permanent magnets consists of a first even number of permanent magnets; and
the second plurality of permanent magnets consists of a second even number of permanent magnets.

3. The furniture apparatus of claim 2, wherein:
a first set of permanent magnets of the first plurality of permanent magnets consists of a first half of the first even number of permanent magnets;
a second set of permanent magnets of the first plurality of permanent magnets consists of a second half of the first even number of permanent magnets;
a north pole of each of the permanent magnets of the first set of permanent magnets is facing away from the non-magnetic base; and
a south pole of each of the permanent magnets of the second set of permanent magnets is facing toward the non-magnetic base.

4. The furniture apparatus of claim 3, wherein:
each of the permanent magnets of the first set of permanent magnets is disposed on a first side of the first non-magnetic ring structure; and
each of the permanent magnets of the second set of permanent magnets is disposed on a second side of the first non-magnetic ring structure;
the second side is opposite the first side.

5. The furniture apparatus of claim 4, wherein:
the first plurality of permanent magnets are disposed in the first non-magnetic ring structure, such that each of the permanent magnets of the first plurality of permanent magnets has an upper portion disposed above an upper surface of the first non-magnetic ring structure, a lower portion disposed below a lower surface of the first non-magnetic ring structure, and a central portion disposed between the upper surface and the lower surface of the first non-magnetic ring structure.

6. The furniture apparatus of claim 5, wherein:
the first non-magnetic ring structure has a first outer diameter; and
the second non-magnetic ring structure has a second outer diameter that is the same as the first outer diameter.

7. The furniture apparatus of claim 6, wherein:
the first non-magnetic ring structure has a first inner diameter; and
the second non-magnetic ring structure has a second inner diameter that is the same as the first inner diameter.

8. The furniture apparatus of claim 7, wherein:
both the first outer diameter and the second outer diameter are less than thirty inches; and
both the first inner diameter and the second inner diameter are less than twenty-four inches.

9. The furniture apparatus of claim 8, wherein:
the non-magnetic base is made of wood;
the non-magnetic support structure is made of wood;
the first non-magnetic ring structure is made of wood;
the second non-magnetic ring structure is made of wood;
the first plurality of permanent magnets consists of ten permanent magnets; and
the second plurality of permanent magnets consists of ten permanent magnets.

10. The furniture apparatus of claim 9, further comprising:
a non-magnetic spacer ring structure, wherein:
the non-magnetic spacer ring structure has a third outer diameter less than both the first outer diameter and the second outer diameter;
a third plurality of permanent magnets disposed at regular intervals in the non-magnetic spacer ring structure; and
the third plurality of permanent magnets comprises less than or equal to four permanent magnets.

11. The furniture apparatus of claim 3, wherein:
the first set of permanent magnets and the second set of permanent magnets are arranged on the first non-magnetic ring structure, such that none of the permanent magnets of the first set of permanent magnets are disposed directly next to one another and none of the permanent magnets of the second set of permanent magnets are disposed directly next to one another.

* * * * *